United States Patent
Ashida

(10) Patent No.: US 10,357,166 B2
(45) Date of Patent: Jul. 23, 2019

(54) ELECTRONIC BLOOD PRESSURE MONITOR AND CONNECTED CUFF TYPE DETERMINATION METHOD

(71) Applicant: OMRON HEALTHCARE CO., LTD., Muko-shi, Kyoto (JP)

(72) Inventor: Tameo Ashida, Kyoto (JP)

(73) Assignee: OMRON HEALTHCARE CO., LTD., Muko-shi (JP)

( * ) Notice: Subject to any disclaimer, the term of this patent is extended or adjusted under 35 U.S.C. 154(b) by 393 days.

(21) Appl. No.: 15/205,808

(22) Filed: Jul. 8, 2016

(65) Prior Publication Data

US 2016/0317051 A1 Nov. 3, 2016

Related U.S. Application Data

(63) Continuation of application No. PCT/JP2015/051768, filed on Jan. 23, 2015.

(30) Foreign Application Priority Data

Feb. 6, 2014 (JP) ................. 2014-021258

(51) Int. Cl.
*A61B 5/022* (2006.01)
*A61B 5/00* (2006.01)

(52) U.S. Cl.
CPC .......... *A61B 5/02233* (2013.01); *A61B 5/022* (2013.01); *A61B 5/7246* (2013.01);
(Continued)

(58) Field of Classification Search
CPC ........................................ A61B 5/022–0235
See application file for complete search history.

(56) References Cited

U.S. PATENT DOCUMENTS 5,060,654 A * 10/1991 Malkamaki ........ A61B 5/02141
600/490
2006/0293601 A1 * 12/2006 Lane .................... A61B 5/0225
600/495
2009/0099466 A1 * 4/2009 Wong ................. A61B 5/02141
600/495

FOREIGN PATENT DOCUMENTS

JP H06-125880 A 5/1994
JP 2008-546478 A 12/2008
(Continued)

OTHER PUBLICATIONS

Apr. 21, 2015 International Search Report issued in International Patent Application No. PCT/JP2015/051768.

*Primary Examiner* — Thaddeus B Cox
(74) *Attorney, Agent, or Firm* — Oliff PLC

(57) ABSTRACT

A blood pressure monitor includes a cuff and main unit. The cuff includes a fluid bladder, tube, and approximately cylindrical plug attached to a leading end of the tube, and a through-hole is provided in peripheral wall of plug. An inner diameter of a part of plug further on leading end side of plug than through-hole is set variably, in accordance with the type of cuff, to a diameter≤inner diameter of a part of plug aside from part further on leading end side. Main unit includes a plug receiving portion that communicates with pump via a pipe, a first pressure sensor that detects pressure in pipe, second pressure sensor that detects an inner pressure of plug inserted into plug receiving portion, and cuff type determining unit that determines type of cuff connected to main unit on basis of difference between pressures detected by first and second pressure sensor.

17 Claims, 14 Drawing Sheets

(52) U.S. Cl.
   CPC ................ *A61B 2560/0266* (2013.01); *A61B 2562/0247* (2013.01)

(56)  References Cited

FOREIGN PATENT DOCUMENTS

JP        2012-205719 A    10/2012
   WO        2010/073689 A1    7/2010

* cited by examiner

ELECTRONIC BLOOD PRESSURE MONITOR AND CONNECTED CUFF TYPE DETERMINATION METHOD

TECHNICAL FIELD

This invention relates to electronic blood pressure monitors, and particularly relates to an electronic blood pressure monitor capable of determining the type of a cuff connected to a main unit.

This invention also relates to a cuff type determination method for determining the type of a cuff connected to a main unit in such an electronic blood pressure monitor.

BACKGROUND ART

As a conventional example of this type of blood pressure measurement device, Patent Literature 1 (JP 2008-546478A) discloses a device configured so that a lumen (a conduit) that connects a cuff and a main unit is connected to two ports provided in the main unit (see FIGS. 2 and 3 of Patent Literature 1). According to this device, it is determined whether the connected cuff is a dual-layer lumen cuff or a single-layer lumen cuff by determining whether or not there is a unique difference in pressure near the respective two ports at the beginning of a period in which the cuff is inflated.

CITATION LIST

Patent Literature

Patent Literature 1: JP 2008-546478A

SUMMARY OF INVENTION

Technical Problem

However, according to the above-describe device, it is necessary to connect the lumen (a conduit for supplying and exhausting a fluid to and from the accompanying cuff) to the two ports of the main unit regardless of whether the cuff is a dual-layer lumen cuff or a single-layer lumen cuff. There is thus a problem in that the task of connecting the main unit and the lumen is unavoidably complicated in situations where the device is actually used. In addition, the difference between the pressures near the two ports detected by the aforementioned device is primarily produced by resistance that a pressurized fluid sent, to the lumen from one of the ports by a pump is subjected to within the lumen. As such, the magnitude of this resistance changes depending on the length of the lumen that connects the one port to the other port, as well as the shape of the lumen during pressure measurement and the like. If the lumen is twisted greatly, bent, or the like, for example, the device may produce an erroneous determination.

Accordingly, this invention provides an electronic blood pressure monitor capable of accurately determining the type of a connected cuff using a simple configuration.

This invention also provides a cuff type determination method that automatically determines the type of a cuff connected to a main unit in the aforementioned electronic blood pressure monitor.

Solution to Problem

To solve the aforementioned problems, an electronic blood pressure monitor according to an aspect of this invention is an electronic blood pressure monitor including a cuff that pressurizes a measurement area and a main unit that measures a pressure in the cuff and calculates a blood pressure in the measurement area on the basis of a result of the measurement, wherein the cuff includes:
a fluid bladder;
a tube that communicates with the fluid bladder; and
an approximately cylindrical plug, attached to a leading end of the tube, that is to be inserted into the main unit to supply a fluid to the fluid bladder, and
a through-hole is provided in a peripheral wall of the plug;
an inner diameter of a part of the plug further on a leading end side of the plug than the through-hole is set variably, in accordance with a type of the cuff, to a diameter less than or equal to an inner diameter of a part of a plug aside from the part further on the leading end side, and
the main unit includes:
a plug receiving portion that communicates with a pump within a housing of the main unit via a pipe;
a first pressure sensor that detects a pressure in the pipe;
a second pressure sensor that detects an inner pressure of the plug inserted into the plug receiving portion, through the through-hole in the plug; and
a cuff type determining unit that determines the type of the cuff connected to the main unit on the basis of a difference between the pressures detected by the first pressure sensor and the second pressure sensor.

In the electronic blood pressure monitor according to this aspect of the invention, the cuff is connected to the main unit via the plug, which has a substantially cylindrical shape and in a peripheral all of which the through-hole is provided. Here, the inner diameter of the part of the plug further on the leading end side of the plug than the through-hole when the cuff is connected to the main unit is set variably, in accordance with the type of the cuff, to a diameter less than or equal to the inner diameter of a part of a plug aside from the part further on the leading end side. On the other hand, the plug receiving portion (connector) provided in the main unit communicates with the pump and the first pressure sensor via the pipe, and communicates with the second pressure sensor for detecting the inner pressure of the plug via the through-hole (detection hole) provided in the peripheral wall of the plug. The first pressure sensor detects the pressure in the pipe, and the second pressure sensor detects the inner pressure of the plug. The inner diameter of the part of the plug further on the leading end side of the plug than the through-hole is set variably in accordance with the type of the cuff as described above, and thus a difference between the pressure in the pipe and the inner pressure of the plug changes in accordance with the type of the cuff. Using this, the cuff type determining unit determines the type of the cuff connected to the main unit on the basis of a difference between the pressures detected by the two sensors. In this manner, the electronic blood pressure monitor according to this aspect of the invention can automatically determine the type of the cuff with ease, using a simple configuration. In addition, the difference between the two to pressures used in the determination in this method is not easily affected by the fluid bladder of the cuff, the tube connected to the cuff, or the like, and thus an accurate cuff type determination can be made under all usage conditions. Although the type of the cuff includes differences in the capacity of the fluid bladder contained in the cuff, differences in the size of a band-shaped body containing the fluid bladder, and so on, the type is not limited thereto.

An electronic blood pressure monitor according to an aspect may further include a sealing member that seals a gap between a part of an outer circumferential surface of the plug located further on the leading end side of the plug than the through-hole and an tuner circumferential surface of the plug receiving portion in an airtight manner.

With the electronic blood pressure monitor according to this aspect, the airtight sealing effect of the sealing member keeps the pressure in the gap between the outer circumferential surface of the plug and the inner circumferential surface of the plug receiving portion substantially the same as the inner pressure of the plug. Accordingly, the second pressure sensor can find the inner pressure of the plug by detecting the pressure in the gap, which makes it easy to detect the inner pressure of the plug.

In an electronic blood pressure monitor according to an aspect, the inner diameter of the part of the plug further on the leading end side of the plug than the through-hole may be set variably in accordance with a capacity of the fluid bladder contained in the cuff.

With the electronic blood pressure monitor according to this aspect, the capacity of the fluid bladder in the connected cuff can be determined. As such, according to this aspect, the cuff can be inflated and/or deflated as appropriate for the capacity, on the basis of the determination result. This also makes it possible to optimize a blood pressure measurement algorithm on the basis of the magnitude of the determined capacity. For example, in the case where it is determined that the capacity to of the fluid bladder in the cuff is low, the connected cuff can be determined to be a cuff for a child, and a blood pressure measurement algorithm can be optimized by changing the blood pressure measurement algorithm to a blood pressure measurement algorithm for a child. Likewise, in the case where it is determined that the capacity of the fluid bladder in the cuff is high, the blood pressure measurement algorithm can be optimized by changing the blood pressure measurement algorithm to a blood pressure measurement algorithm for an adult.

In an electronic blood pressure monitor according to an aspect, the cuff type determining unit may determine the type of the cuff en the basis of a difference between the detected pressures when a change over time in the difference between the pressures, arising due to the pump starting to inflate the cuff, is in a plateau state.

With the electronic blood pressure monitor according to this aspect, the cuff type is determined on the basis of a difference between the pressures in a plateau state, in which the difference between the pressure in the pipe and the inner pressure of the plug is pronounced and stable, when the cuff is inflated by the pump, and thus the cuff type can be accurately determined.

In an electronic blood pressure monitor according to an aspect, the cuff type determining unit may carry out the determination by comparing a difference between the pressures detected by the first pressure sensor and the second pressure sensor with a predetermined threshold.

With the electronic blood pressure monitor according to this aspect, the aforementioned pressure difference is compared with a threshold and the cuff type is determined on the basis of a magnitude relationship between the two. Accordingly, the electronic, blood pressure monitor can determine the type of the connected cuff through an extremely simple computation.

Another aspect of this invention is a cuff type determination method that determines a type of a cuff connected to the main unit in the electronic blood pressure monitor according to the above aspects, the method including:

a step of driving the pump to start inflating the cuff;

a step of detecting a pressure within the pipe using the first pressure sensor and detecting an inner pressure in the plug using the second pressure sensor during inflation; and a step of the cuff type determining unit determining the type of the connected cuff on the basis of a difference in the pressures detected by the first pressure sensor and the second pressure sensor in the step of detecting.

With the cuff type determination method according to this other aspect of the invention, the first pressure sensor detects the pressure in the pipe (the pinup discharge pressure) and the second pressure sensor detects the inner pressure of the plug when the pump inflates the cuff. The cuff type determining unit then determines the type of the connected cuff on the basis of a difference between the two pressures obtained in this manner. This method makes it possible to determine the cuff type through a simple process alone, and can be carried out during normal cuff inflation. As such, an electronic blood pressure monitor employing this method can quickly determine the type of the connected cuff without being noticed by a user. In other words, according to this method, the automatic cuff type determination process itself can be made unnoticeable to the user. In addition, as described above, the difference between the two pressures used in the determination in this method is not easily affected by the fluid bladder of the cuff, the tube connected to the cuff, or the like, and thus an accurate cuff type determination can be consistently made under all usage environments.

Advantageous Effects of Invention

As is clear from the above, an aspect of this invention provides an electronic blood pressure monitor capable of accurately determining the type of a connected cuff using a simple configuration.

Furthermore, another aspect of this invention provides a cuff type determination method that automatically determines the type of a cuff connected to a main unit in the aforementioned electronic blood, pressure monitor.

DESCRIPTION OF EMBODIMENTS

Hereinafter, an embodiment of this invention will be described in detail with reference to the drawings.

Figure 1:
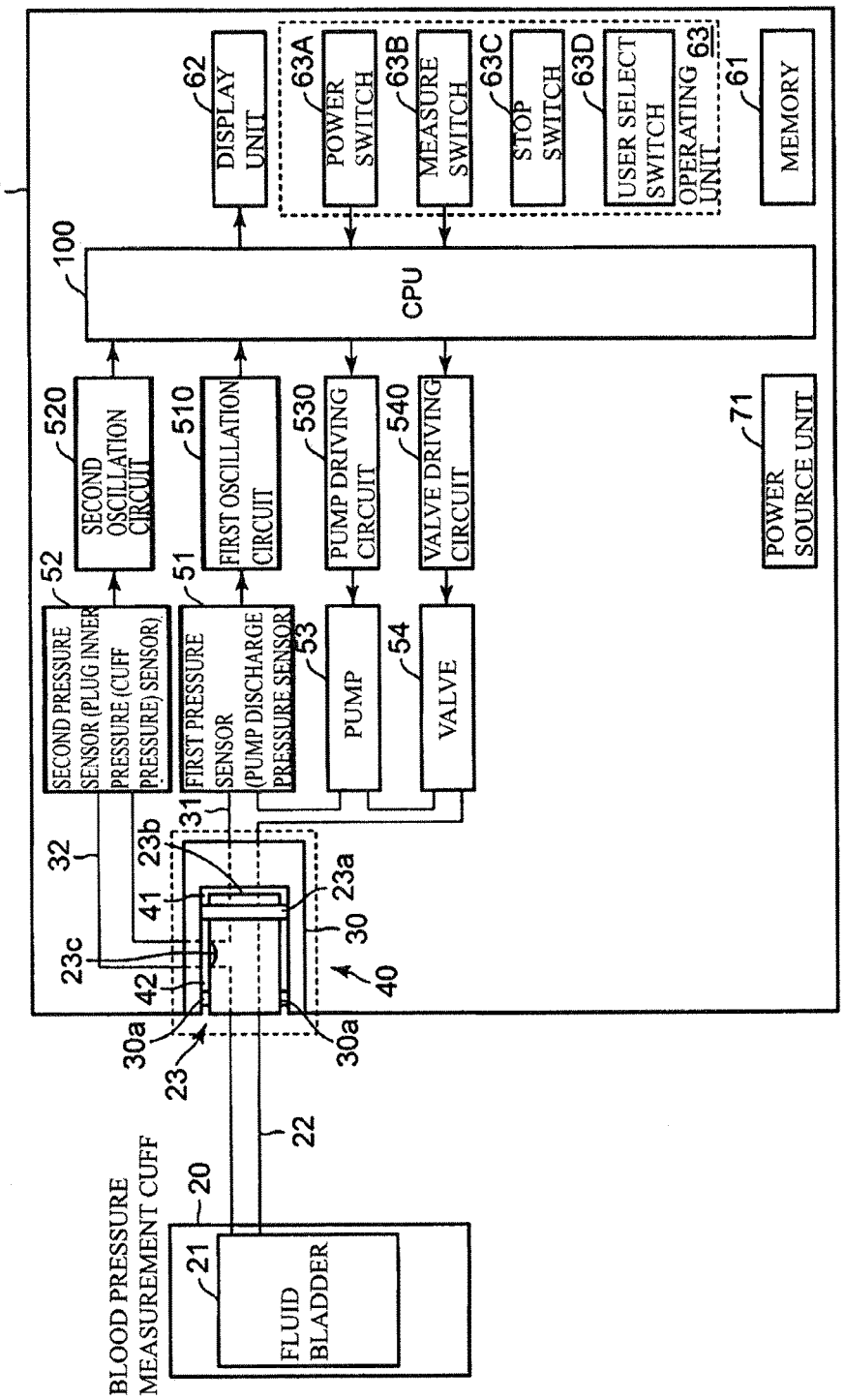
FIG. 1 is a diagram schematically illustrating the configuration of an electronic blood pressure monitor according to an embodiment of this invention.

FIG. 1 is a diagram schematically illustrating the configuration of an electronic blood pressure monitor (indicated overall by reference numeral it according to an embodiment of this invention. This blood pressure monitor 1 includes a main unit 10 and a cuff 20; the cuff 20 is affixed to a measurement area and pressurizes the measurement area, and the main unit 10 measures a pressure of the cuff and calculates a blood pressure on the basis of a result of the measurement.

The culls 20 contains a fluid bladder 21, and a tube 22 for supplying and exhausting a fluid is connected to the fluid bladder 21. A substantially cylindrical plug 23 is connected to another end of the tube 22. A fluid supply/exhaust opening 23b is provided in the plug 23 in an area located in a leading end portion on the main unit side when the plug 23 is connected to the main unit 10, and a through-hole (a detection hole 23c) is provided in a peripheral wall of the substantially cylindrical shape. The cuff 20 and the main unit 10 are connected by inserting the plug 23 into a plug receiving portion (a connector 30) that is provided in the main unit 10 and corresponds to the plug 23; in this connected state, a fluid can flow between the plug 23 and the connector 30. The plug 23 of the cuff 20 and the connector 30 of the main unit 10 constitute a cuff-main unit connection portion 40.

In the connection portion 40 constituted by the plug 23 and the connector 30, a sealing member (an O-ring 23a) provided in the plug 23 and a sealing member (an O-ring 30a) provided in the connector 30 seal a gap between an outer circumferential surface of the plug 23 and an inner circumferential surface of the connector 30 in an airtight manner. The O-ring 23a is provided closer to a leading end side of the plug 23 than the detection hole 23c, and seals a region 41 near an inner base of the connector 30 in an airtight manner. The O-ring 30a is provided in an area on an entry side of the inner circumferential surface of the connector 30 (an area that is closer to the entry side than the detection hole 23c when the plug 23 is inserted into the connector 30), and seals a region 42 enclosed between an inside wall of the connector 30 and an outside wall of the plug 23 so as to be airtight with respect to the exterior and the region 41. Note that the O-ring 23a that defines the region 41 near the inner base of the connector 30 may be provided in the connector 30. Likewise, the O-ring 30a that defines a border between the exterior and the region 42 may be provided in the plug 23.

The main unit 10 is enclosed in a housing, and includes, within the housing, a CPU (central processing unit) 100 serving as a control unit, a display unit 62, a memory 61 serving as a storage unit, an operating unit 63, a power source unit 71, a pump 53, and a valve 54, as well as a first, pressure sensor 51 and a second pressure sensor 52. The main unit 10 also includes a first oscillation circuit 510 that converts an output from the first pressure sensor 51 into a frequency, a second oscillation circuit. 520 that converts an output from the second pressure sensor 52 into a frequency, a pinup driving circuit 530 that drives the pump 53, and a valve driving circuit 540 that drives the valve 54. The pump 53 supplies air to the fluid bladder 21 of the cuff 20 through a first pipe 31, the fluid supply/exhaust hole 23b of the connection portion 40, and the tube 22 so as to increase a pressure within the fluid bladder 21 (a cuff pressure). The valve 54 opens and closes to control the cuff pressure by exhausting or trapping air from or in the fluid bladder 21 through the tube 22, the fluid supply/exhaust hole 23b of the connection portion 40, and the first pipe 31. The pump driving circuit 530 drives the pump 53 on the basis of a control signal supplied from the CPU 100. The valve driving circuit 540 opens and closes the valve 54 on the basis of a control signal supplied from the CPU 100.

The first pressure sensor (a pump discharge pressure sensor) 51 is connected to the first pipe 31 to which the pump 53 and the valve 54 are connected, and detects a pressure within the first pipe 31. The first pressure sensor 51 can therefore detect a pressure in the region 41 of the connection portion 40. When the pump 53 is driven, the pressure in the region 41 detected by the first pressure sensor 51 is substantially the same as the discharge pressure of the pump 53.

Note that the first pressure sensor 51 is a piezoresistance-type pressure sensor, for example. In this example, the first oscillation circuit 510 oscillates on the basis of the value of an electrical signal, from the first pressure sensor 51, that is based on a change in an electrical resistance produced by a piezoresistance effect, and outputs, to the CPU 100, a frequency signal having a frequency based on the value of the electrical signal from the first pressure sensor 51.

A different pipe from the fast pipe 31 (that is, a second pipe 32) is connected to the connector 30; one end of the second pipe 32 is connected to the second pressure sensor (a plug inner pressure (cuff pressure) sensor) 52, and another end communicates with the region 42 around the plug 23 through the connector 30 of the connection portion 40. The second pressure sensor 52 can therefore detect a pressure in the region 42 of the connection portion 40. The region 42 communicates with the interior of the plug 23 via the detection hole 23c, and thus the pressure in the region 42 detected by the second pressure sensor 52 is substantially the same as the inner pressure of the plug 23.

The second pressure sensor 52 is also a piezoresistance-type pressure sensor, for example. In this example, the second oscillation circuit 520 oscillates on the basis of the value of an electrical signal, from the second pressure sensor 52, that is based on a change in an electrical resistance produced by a piezoresistance effect, and outputs, to the CPU 100, a frequency signal having a frequency based on the value of the electrical signal from the second pressure sensor 52.

The display unit 62 includes a display panel and display devices such as indicators, and displays predetermined information in accordance with control signals from the CPU 100.

The operating unit 63 includes a power switch 63A that accepts the input of an instruction for turning the power source unit 71 on or off, a measure switch 63B for accepting an instruction to start measuring a blood pressure, a stop switch 63C for accepting an instruction to stop measurement, and a user select switch 63D for selecting a user to serve as a measurement subject from among multiple registered users. These to switches 63A, 63B, 63C, and 63D input operation signals based on instructions made by the user to the CPU 100.

The memory 61 stores data of a program for making a connected cuff determination, which will be described later; data of a correspondence relationship between an inner diameter of (the fluid supply/exhaust hole 23b of) a leading end portion of the plug 23 (in other words, a differential pressure, which will be described later) and the type of the cuff; and data of a program fir controlling the blood pressure monitor 1; as well as data used to control the blood pressure monitor 1. The memory 61 also stores configuration data for configuring various types of functions of the blood pressure monitor 1, data of blood pressure value measurement results, and so on. The memory 61 is also used as a working memory when programs are executed.

Operating as a cuff pressure control unit in accordance with a program stored in the memory 61 for controlling the blood pressure monitor 1, the CPU 100 controls the driving of the pump 53, the valve 54 and the like in accordance with operation signals from the operating unit 63. Furthermore, in addition to calculating a blood pressure value on the basis of a signal from the first pressure sensor 51 and controlling the display unit 62 and the memory 61, the CPU 100 operates as a cuff type determining unit in accordance with a program stored in the memory 61 for determining the connected cuff, and controls the first pressure sensor 51, the second pressure sensor 52, and the like while controlling the driving of the pump 53, the valve 54, and the like. The CPU 100 operating as the cuff type determining unit determines the type of the cuff 20 that is connected, on the basis of signals from the first pressure sensor 51 and the second pressure sensor 52.

Note that the inner diameter of (the fluid supply/exhaust hole 23b of) the leading end portion of the plug 23 is set variably in accordance with the type of the cuff; more specifically, the inner diameter is set selectively on the basis of the type of the cuff, in accordance with a predetermined correspondence relationship between the inner diameter and the type of the cuff. The type of the cuff is defined, for example, by the capacity of the fluid bladder 21 that the cuff 20 contains. In this ease, the memory 61 stores data of a correspondence relationship between the inner diameter the differential pressure, described later) and the capacity of the fluid bladder 21 as a correspondence relationship between the inner diameter of (the fluid supply/exhaust hole 23b of) the leading end portion of the plug 23 (in other words, the differential pressure, which will be described later) and the type of the cuff, and the inner diameter of (the fluid supply/exhaust bole 23b of) the leading end portion of the plug 23 is set selectively in accordance with the capacity of the fluid bladder 21. As such, in this case, the cuff type determining unit can determine the capacity of the fluid bladder 21 in the connected cuff 20 on the basis of a result of the cult type determination. Therefore, on the basis of the determination result, the electronic blood pressure monitor 1 can inflate and/or deflate as appropriate for the capacity. This also makes it possible to optimize a blood pressure measurement algorithm on the basis of the magnitude of the determined capacity. For example, in the case where it is determined that the capacity of the fluid bladder 21 of the connected cuff 20 is low (that the capacity corresponds to a cuff for a child), the connected cull can be determined to be a cuff for a child, and the blood pressure measurement algorithm can then be optimized by changing the blood pressure measurement algorithm to a blood pressure measurement algorithm for a child. Likewise, in the case where it is determined that the capacity of the fluid bladder 21 of the connected cuff 20 is high (that the capacity corresponds to a cuff for a typical adult), the blood pressure measurement algorithm can be optimized by changing the blood pressure measurement algorithm to a blood pressure measurement algorithm for an adult.

The power source unit 71 supplies power to the respective elements, namely the CPU 100 the first pressure sensor 51, the pump 53, the valve 54, the display unit 62, the memory 61, the first oscillation circuit 510, the pump driving circuit 530, and the to valve driving circuit 540.

Next, the configuration of the plug 2 will be described with reference to FIGS. 2A, 2B, and 3. The plug 23 includes the fluid supply/exhaust hole 23b, which has an inner diameter that is set selectively in accordance with the type of the cuff.

Figure 2A:
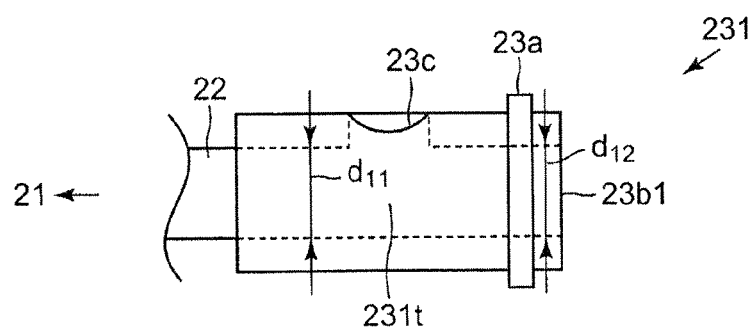
FIG. 2A is a schematic diagram illustrating the configuration of a type connection plug used in the aforementioned electronic blood pressure monitor.

FIG. 2A is a diagram illustrating the overall configuration of a type I plug 231. The type I plug 231 is, for example, a plug 23 used for a cuff having a comparatively high capacity of the fluid bladder 21, that is used for a typical adult. The type I plug 231 has a flow channel 231t that passes through the plug with a uniform inner diameter, and a branch channel leading to the detection hole 23c is formed in a central area of the flow channel 231t. An inner diameter d12 of a fluid supply/exhaust hole 23b1 of the type I plug 231 is the same a an inner diameter d11. The inner diameter d12 is 2.0 millimeters, for example.

Figure 2B:
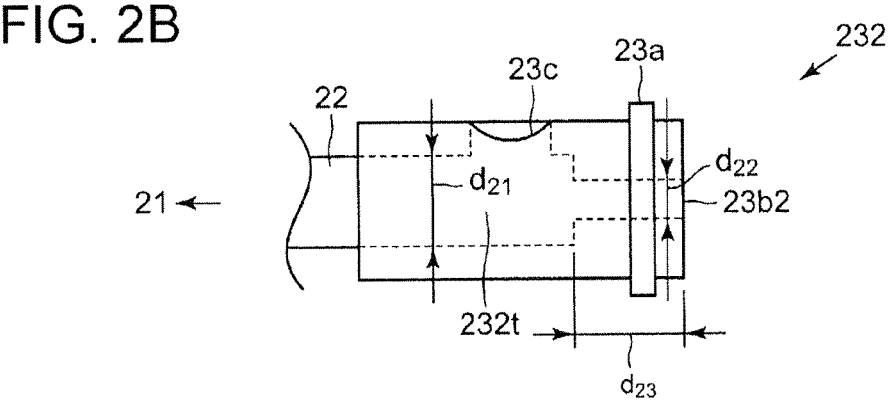
FIG. 2B is a schematic diagram illustrating the configuration of a type connection plug used in the aforementioned electronic blood pressure monitor.

FIG. 2B is a diagram illustrating the overall configuration of a type II plug 232. The type II plug 232 is, for example, a plug 23 used for a cuff having a comparatively low capacity of the fluid bladder 21, that is used for a child. Like the type I plug 231, the branch channel and the detection hole 23c are formed in the type II plug 232; however while the type I plug 231 has the flow channel 231t that passes through the plug with a uniform inner diameter, a flow channel 232t that passes through the plug with a non-uniform inner diameter is formed in the type II plug 232. A tube-side inner diameter d21 of the type II plug 232 may be the same as the inner diameter d11 of the type I plug 231, and a leading end side of the flow channel 232*t* in the type II plug 232 is reduced to an inner diameter d22 for a predetermined length d23 (d12>d22). The inner diameter d22 is 0.8 millimeters, for example. In other words, the type I plug 231 and the type II plug 232 differ in terms of the inner diameters d12 and d22 of the fluid supply/exhaust holes 23*b*1 and 23*b*2.

Figure 3:
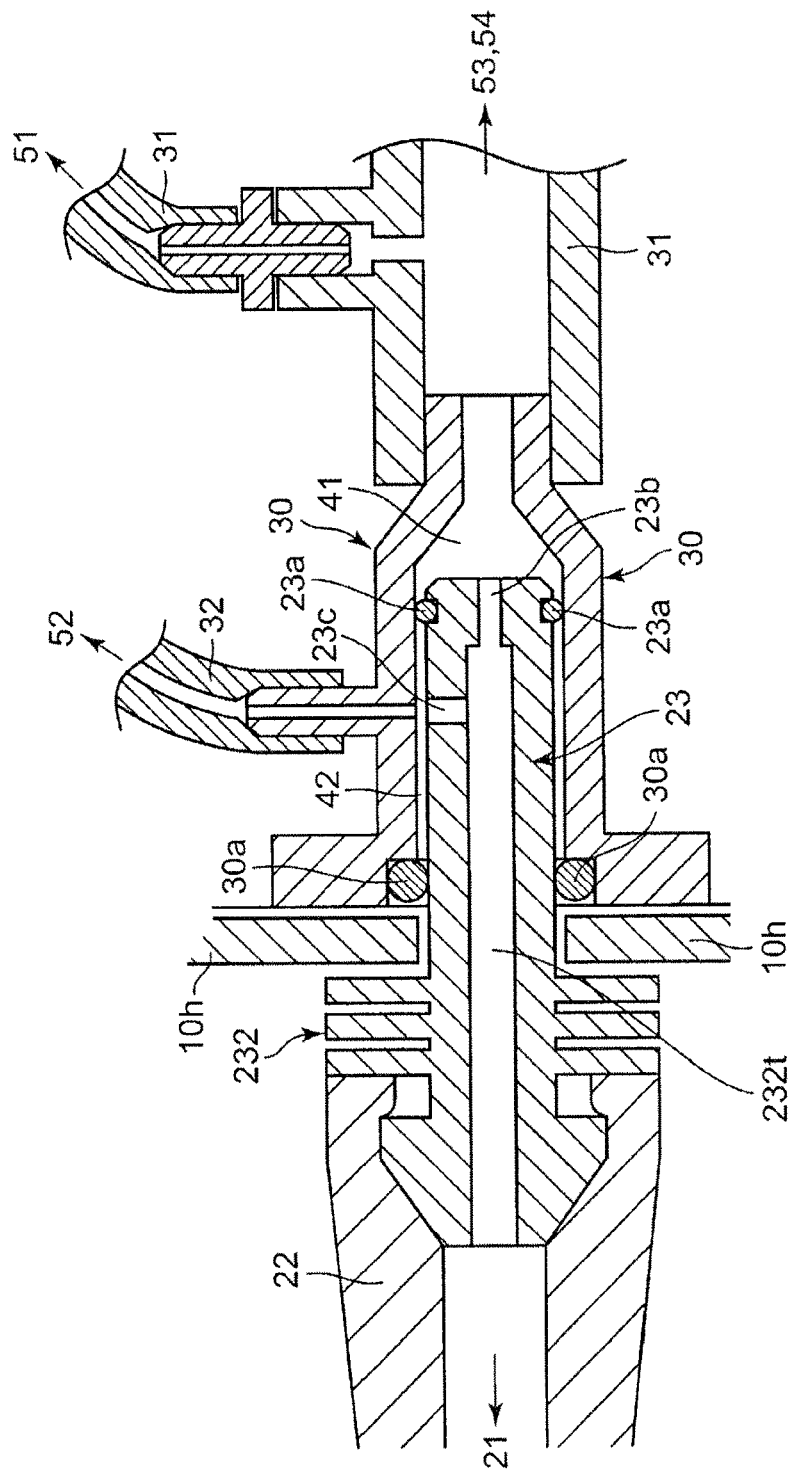
FIG. 3 is an enlarged cross-sectional view of the vicinity of an electronic blood pressure-monitor main unit connection portion, illustrating an example of the specific shape of the aforementioned type II connection plug.

FIG. 3 is an enlarged cross-sectional view of the vicinity of the connection portion 40, illustrating a specific example of the type II plug 232. As described above, when the type II plug 232 is connected to the connector 30, the region 41 and the region 42 are sealed in an airtight manner by the effects of the two sealing members 23*a* and 30*a* (the same applied in the type I plug 231 as well). The region 41 communicates with the first pressure sensor 51, the pump 53, and the valve 54 via the first pipe 31. The region 42 communicates with the second pressure sensor 52 via the second pipe 32. The second pipe 32 communicates with the interior of the type II plug 232 via the detection hole 23*c*. Accordingly, the first pressure sensor 51 detects a pressure in the vicinity of the region 41, and the second pressure sensor 52 detects a pressure in the vicinity of the region 42 (in other words, the inner pressure of the type II plug 232). In the type II plug 232, the inner diameter of the inner flow channel is not uniform, and the fluid supply/exhaust hole 23*b* is formed so that the inner diameter thereof is smaller than other portions. Accordingly, when the pump 53 is driven and a fluid (air, for example) is supplied to the type II plug 232 from the first pipe 31, a loss of pressure occurs in the fluid supply/exhaust hole 23*b*, and the inner pressure of the plug drops below the pressure in the region 41. As opposed to this, there is no corresponding loss of pressure in the type I plug 231 (even if such a loss of pressure does occur, that loss is at least extremely small compared to the loss of pressure occurring in the type II plug 232).

Characteristics of changes in the pressure of the region 41 and the region 42 (the pump discharge pressure and the plug inner pressure) over time in a period of approximately one second from when the pump 53 starts being driven, for the type I plug 231 and the type II plug 232, will be described with reference to FIGS. 4A, 4B, and 5.

Figure 4A:
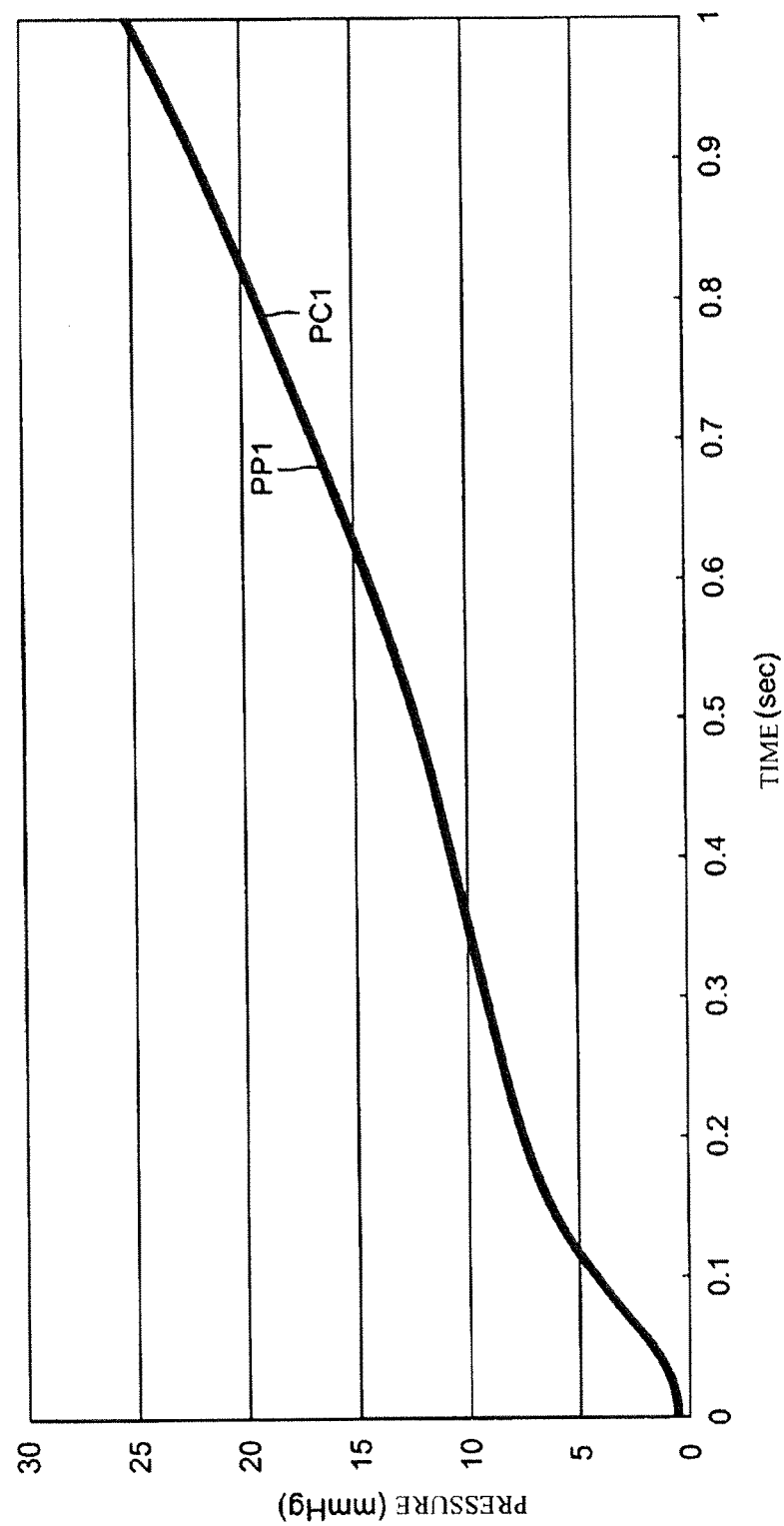
FIG. 4A is a mph illustrating a result of measuring a pump discharge pressure and a cuff pressure (plug inner pressure) in a cuff inflation initial period under predetermined conditions (when a type I connection phi; is used).

FIG. 4A plots changes in a pump discharge pressure PP1 and a plug inner pressure PC1 over time in a period of one second from when the pump 53 starts supplying a fluid (air) at a predetermined flow rate (t=0) to a model cuff having the type I plug 231 (a supply/exhaust hole inner diameter of 2.0 mm) connected to a tube thereof. The model cuff is wrapped around a simulated and having a circumference of 17 centimeters, and is set to a cuff pressure of zero at t=0. The specification of the pump 53 used are three air cylinders, an output rating of DC 6 V, a no-load flow rate of 1.6 L/min, a no-load current of 170 mA, a maximum current of 250 mA, and a maximum pressure of 80 kPa.

As is clear from FIG. 4A, the pump discharge pressure PP1 and the cuff pressure PC1 both change in substantially the same state throughout a period of one second from when the pump 53 starts being driven. In other words, it can be seen that in the case of the type I plug 231, there is no difference between the pressure of the region 41 and the pressure of the region 42 when the pump is driven.

Figure 4B:
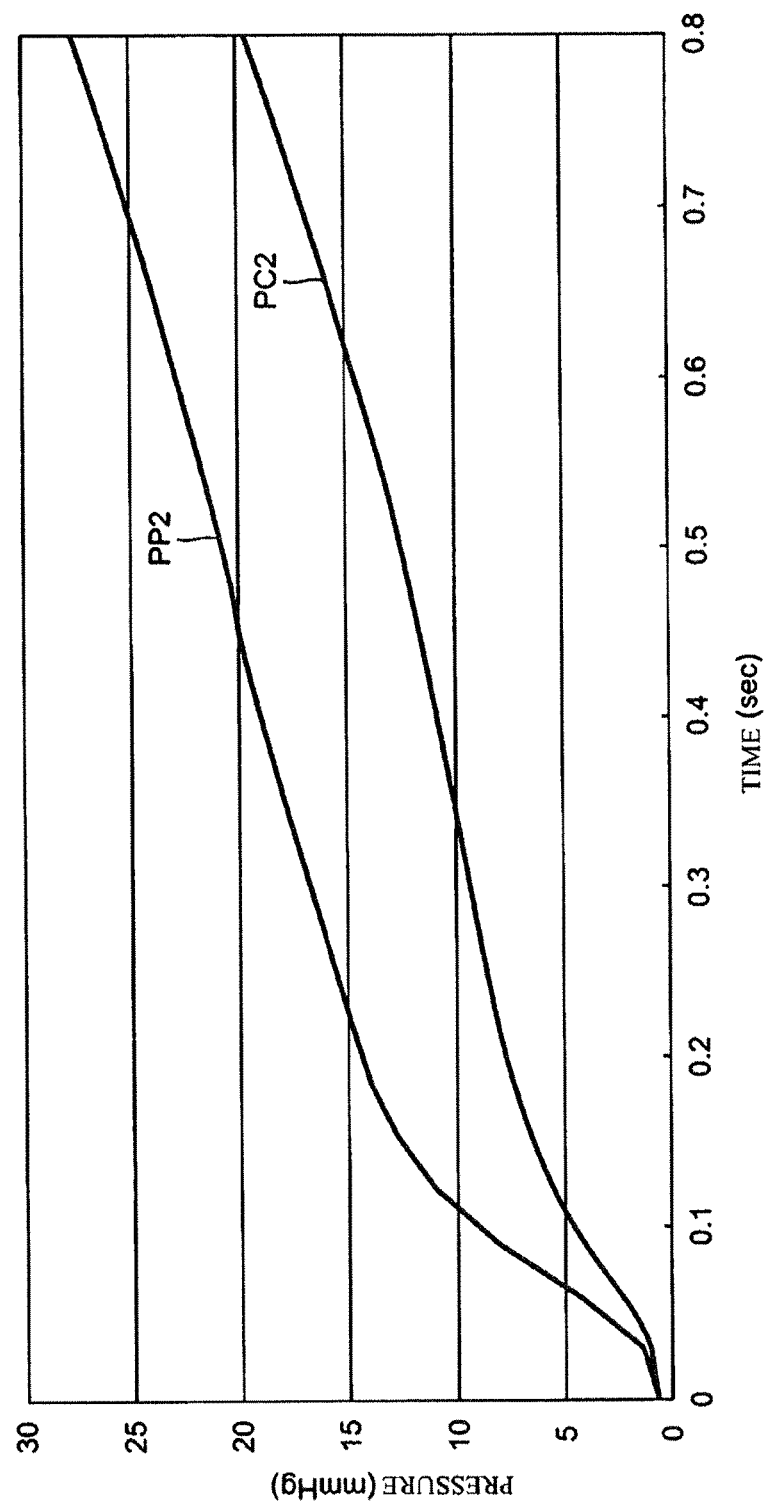
FIG. 4B is a graph illustrating a result of measuring a pump discharge pressure and a cuff pressure (plug inner pressure) in a cuff inflation initial period wider predetermined conditions (when a type II connection plug is used).

FIG. 4B plots changes in a pump discharge pressure PP2 and a plug inner pressure PC2, measured under the same conditions as in FIG. 4A, over time with the type II plan 232 (a supply/exhaust hole inner diameter of 0.8 mm) connected to the model cuff used in the measurement indicated in FIG. 4A.

Unlike in FIG. 4A, it can be seen from FIG. 4B that the pump discharge pressure PP2 and the cuff pressure PC2 are correlated but having different pressures over a period of approximately one second (0.8 seconds, in FIG. 4B) from when the pump 53 starts being driven. In particular, the difference between the two increases for approximately 0.3 seconds from the start of pump driving, and then the pressures increase with a substantially constant difference therebetween. In other words, it can be seen that in the case of the type II plug 232, there is a difference between the pressure of the region 41 and the pressure of the region 42 when the pump is driven.

Figure 5:
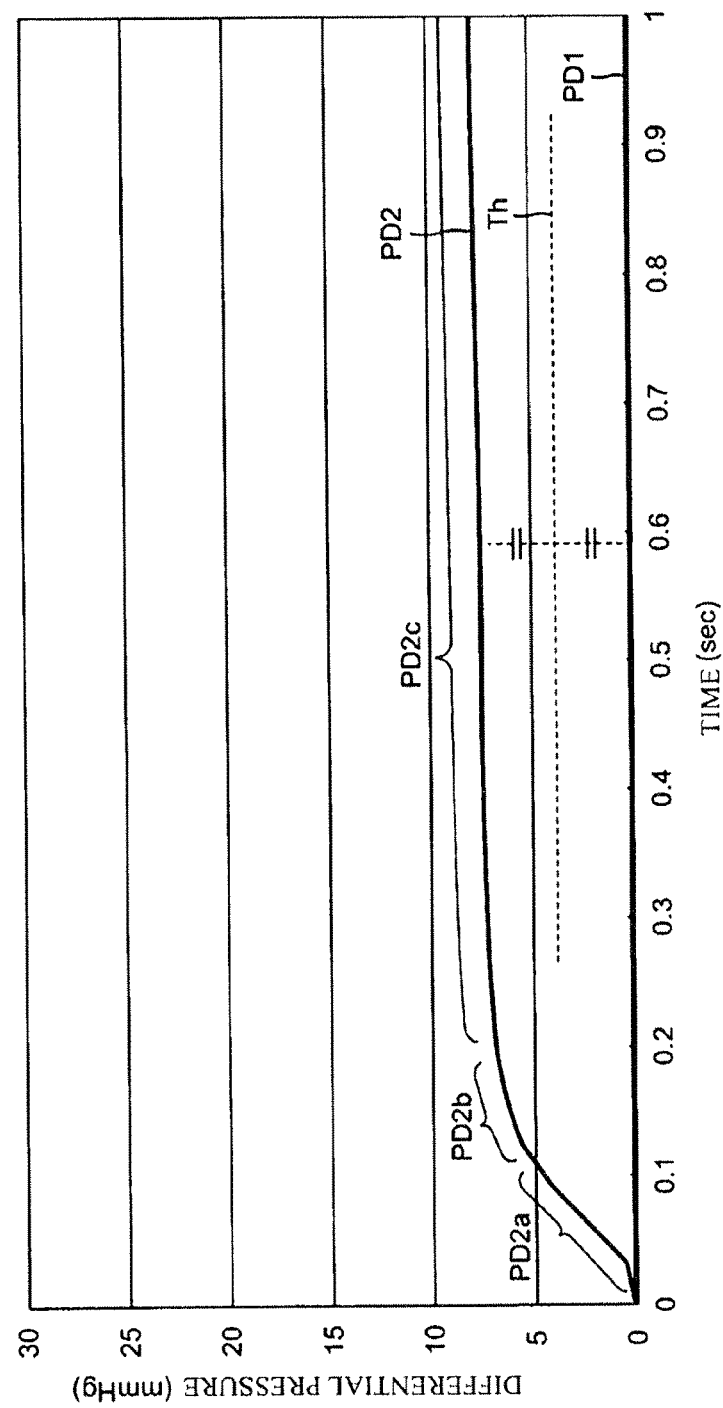
FIG. 5 is a graph illustrating a differential pressure in the cuff inflation initial period when using a type I connection plug and when using a type II connection plug, calculated from the measurement results illustrated in FIGS. 4A and 4B.

FIG. 5 plots differential pressures of the pump discharge pressures PP1 and PP2 and the cuff pressures PC1 and PC2 illustrated in FIGS. 4A and 4B (PD1(=PP1−PC1), PD2 (=PP2−PC2)).

As is clearly indicated in FIG. 5, in the case where air is supplied to the model cuff through the type I plug 231, the differential pressure PD1 remains at substantially zero when that supply starts, however, in the case where air is supplied to the model cuff through the type II plug 232, the differential pressure rises from the start of the supply, increases more gradually from 0.2 to 0.3 seconds following the start, and then stabilizes (plateaus) at a non-zero value (approximately 8 mmHg) from approximately 0.3 seconds and on following the start. A difference of approximately 8 mmHg (PD1 approximately 0.0 mmHg, PD2=approximately 8.0 mmHg) arises between the differential pressure PD1 and the differential pressure PD2 in the plateau state (t=approximately 0.3 and on).

Accordingly, operating as the cuff type determining unit, the CPU 100 finds the differential pressure at a timing where the differential pressure is thought to be in the plateau state, compares the found differential pressure with a predetermined threshold, determines whether the plug 23 connected to the connection portion 40 is type I or type II from a magnitude relationship between the differential pressure and the threshold, and determines the type of the connected cuff by referring to the predetermined correspondence relationship between the inner diameter of the fluid supply/exhaust hole 23*b* and the type of the cuff that is stored. The predetermined threshold may be set to, for example, an intermediate value between the differential pressure PD1 and the differential pressure PD2 in the plateau state, which is Th=4.0 mmHg in the case of FIG. 5.

Although two types of plugs are described as examples of the plug 23, the number of plug types is not limited to two. It is possible to use three or more types of plus. In this case, the cuff type determining unit may store data of differential pressures in the plateau state for each of the supply/exhaust hole inner diameters for the three or more types, measured in advance. Alternatively, the cuff type determining unit may store a plurality of the aforementioned thresholds, measured in advance. It goes without saving that the aforementioned differential pressure values, the time periods in which the aforementioned plateau state appears, and so on change depending to on the inner diameter of the fluid supply/ exhaust hole 23*b* in the leading end portion of the plug 23, the performance of the pump 53, driving conditions, and so on. Accordingly, the aforementioned values are merely examples, and the values are not limited thereto.

The determination of the type of the connected cuff by the cuff type determining unit can be carried out in an initial period of cuff inflation immediately after the start of blood pressure measurement, but the timing at which the cuff type determination is carried out is not limited thereto. The cuff type determination may be carried out when power is supplied to the main unit 10. Alternatively, a means that makes it possible to detect that the cuff 20 has been connected to the main unit 10 may be provided, and the cuff type determination may be carried out upon the cuff 20 being connected. The determination may instead be carried out periodically.

In the aforementioned example, a single cuff type is specified from among a plurality of cuff types having different capacities of the fluid bladder 21, or in other words, the capacity of the fluid bladder 21 is specified. In this case, the determination result can be used to determine an amount of air supplied to the cuff 20 per unit of time during inflation, determine an amount of air exhausted from the cuff 20 per unit of time during deflation, determine whether to carry out a blood pressure measurement process during inflation, during deflation, or during both, optimize the blood pressure measurement algorithm, and so on. However, the plurality of types of cuffs need not have different fluid bladder 21 capacities. For example, the cuffs may have different widths, lengths (circumferences), or the like.

Figure 6:
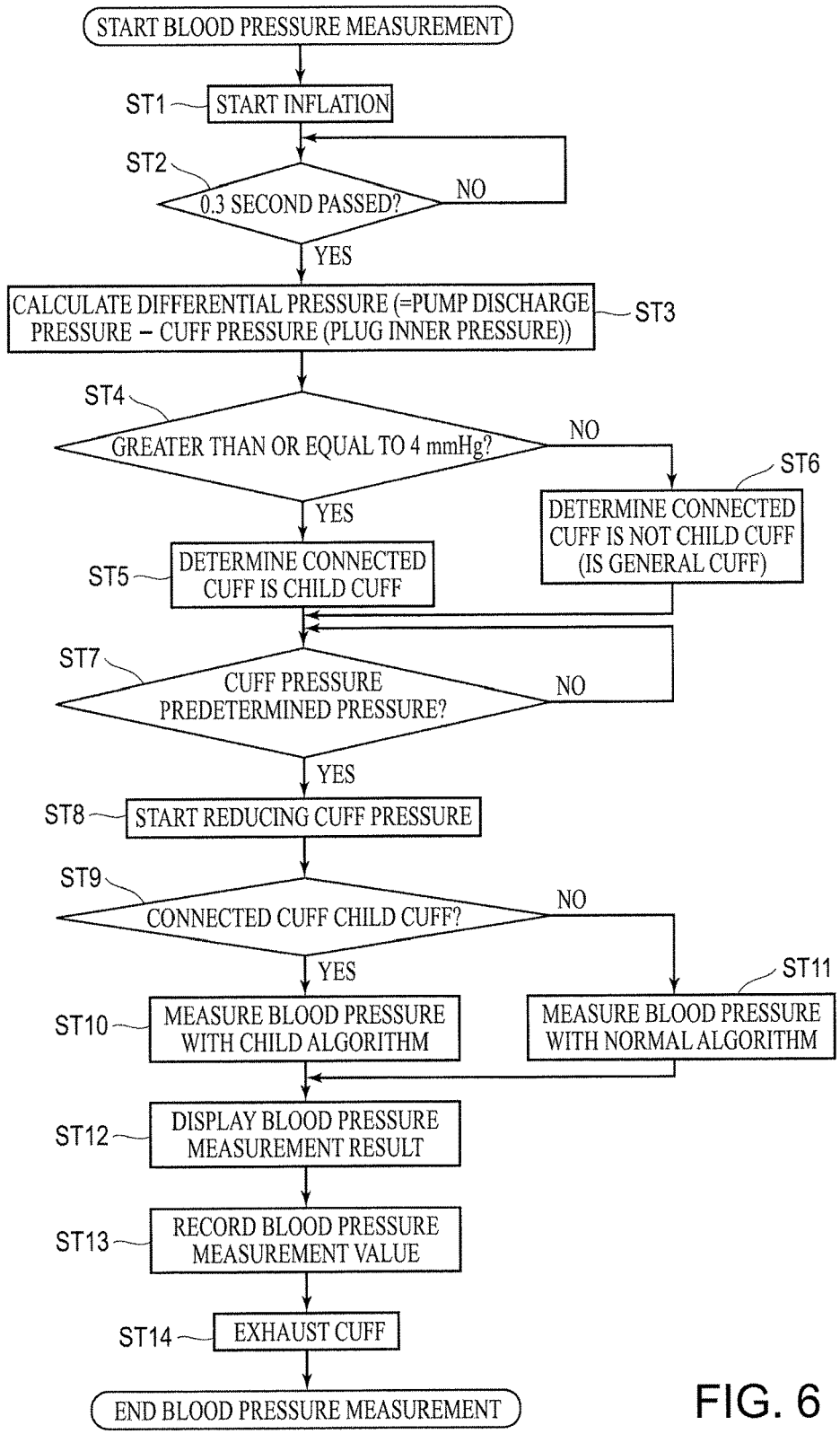
FIG. 6 is a diagram illustrating an overview of a flow of operations performed by the aforementioned electronic blood pressure monitor.
Figure 7:
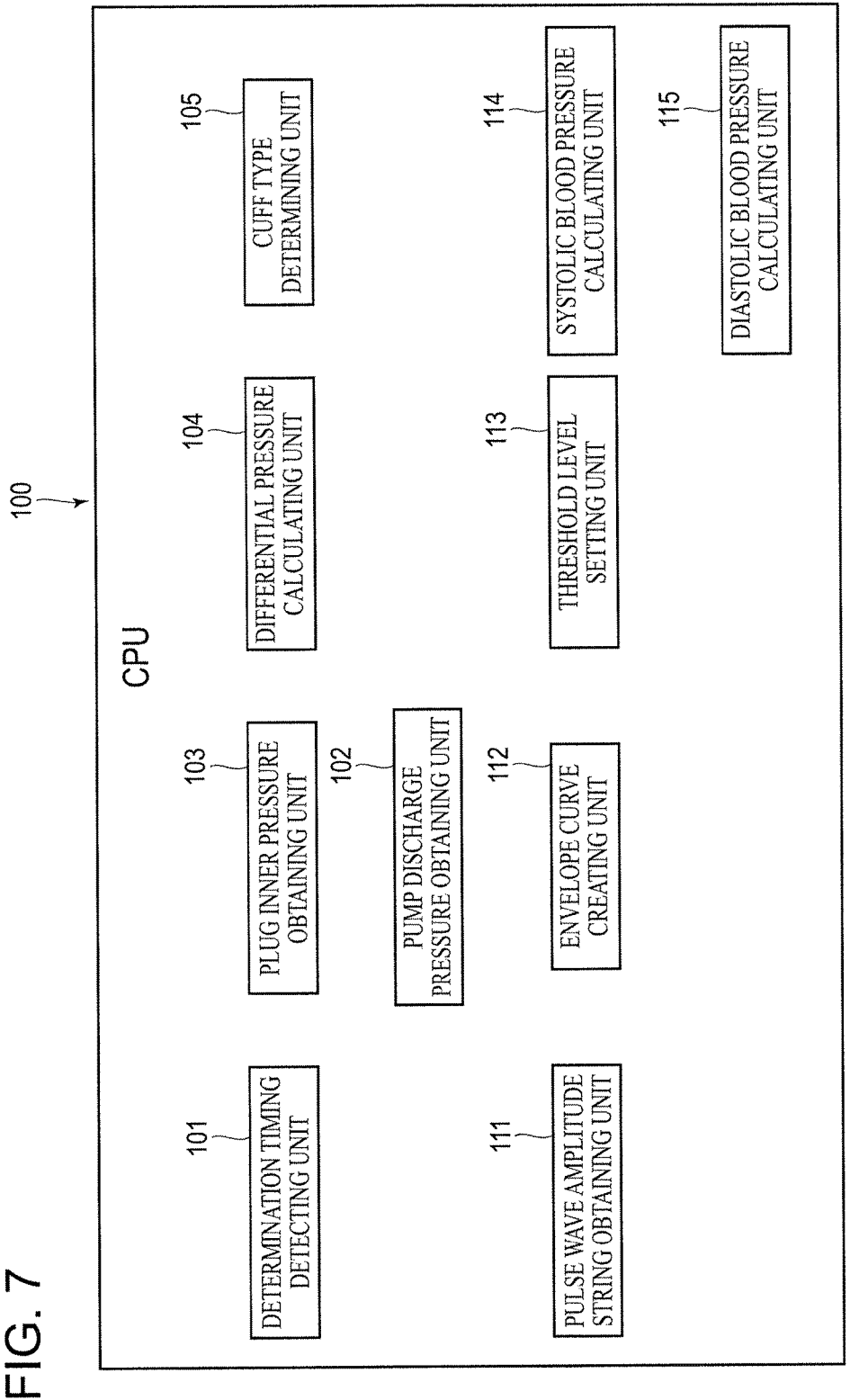
FIG. 7 is a diagram illustrating an example of a set of elements implemented by a CPU (central processing unit) of the aforementioned electronic blood pressure monitor for determining a connected cuff type and calculating a blood pressure value.
Figure 8A:
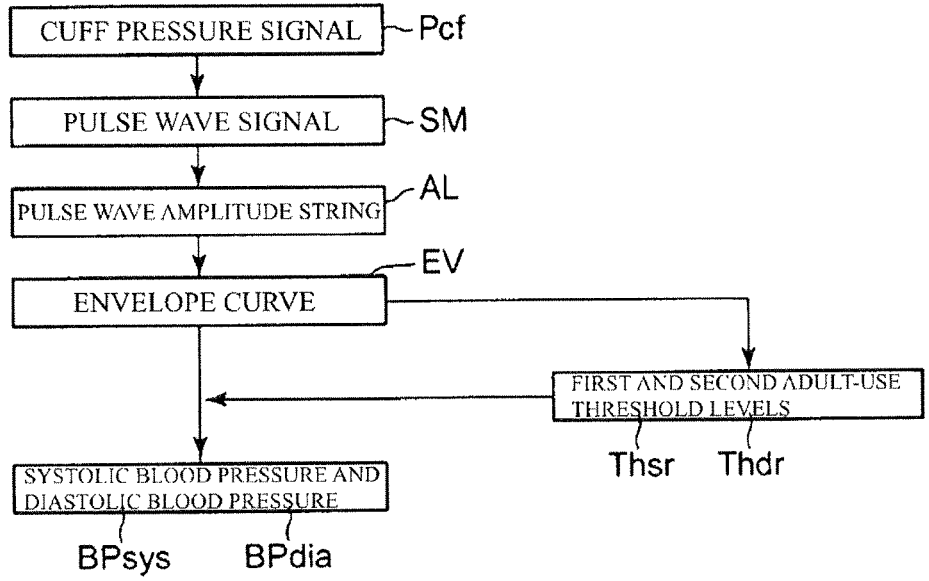
FIG. 8A is a diagram illustrating an example of a process carried out when calculating a blood pressure value using some of the elements illustrated in FIG. 7 (an adult blood pressure calculation process).
Figure 8B:
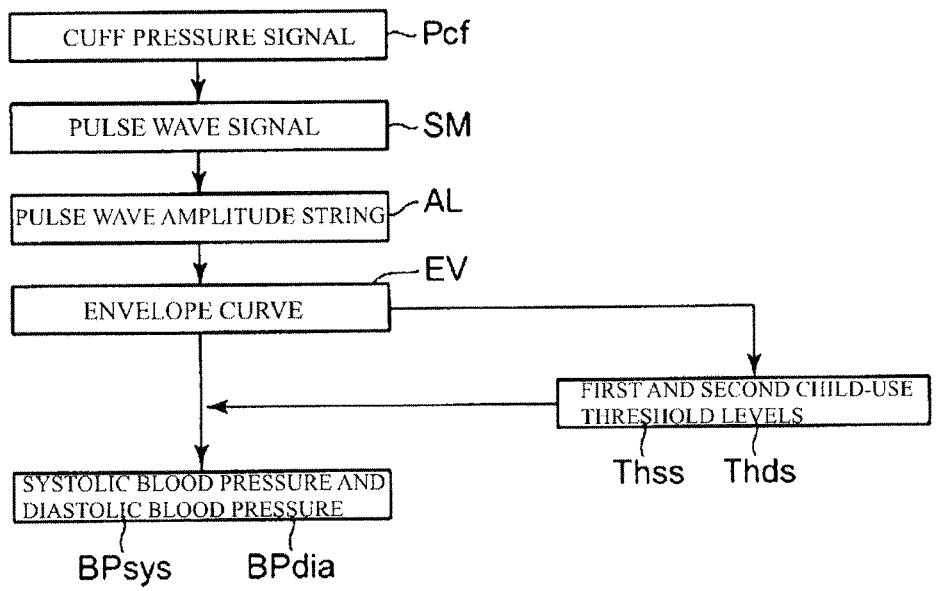
FIG. 8B is a diagram illustrating another example of a process carried out when calculating a blood pressure value using some of the elements illustrated in FIG. 7 (a child blood pressure calculation process).
Figure 9A:
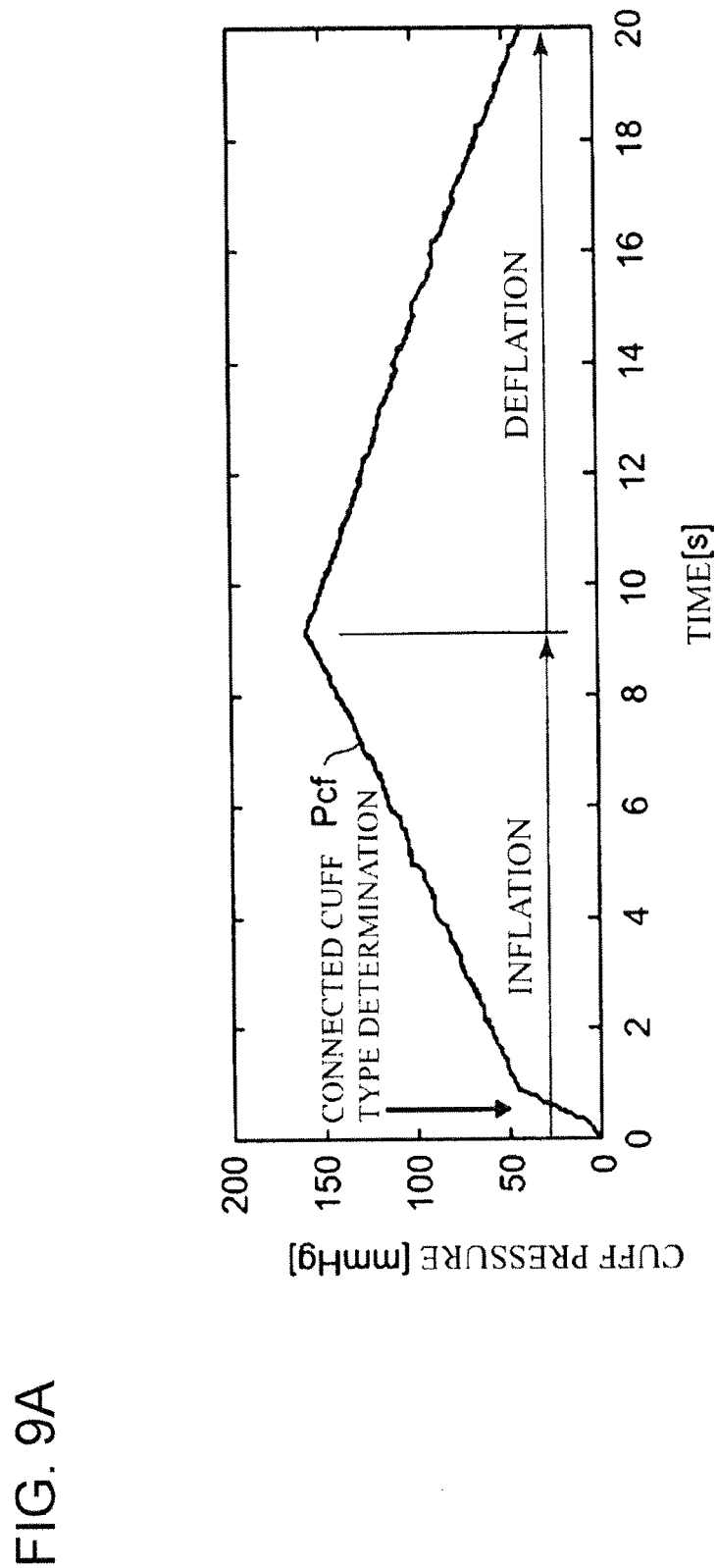
FIG. 9A is a diagram illustrating an example of a cuff pressure signal detected by a second pressure sensor of the aforementioned electronic blood pressure monitor.
Figure 9B:
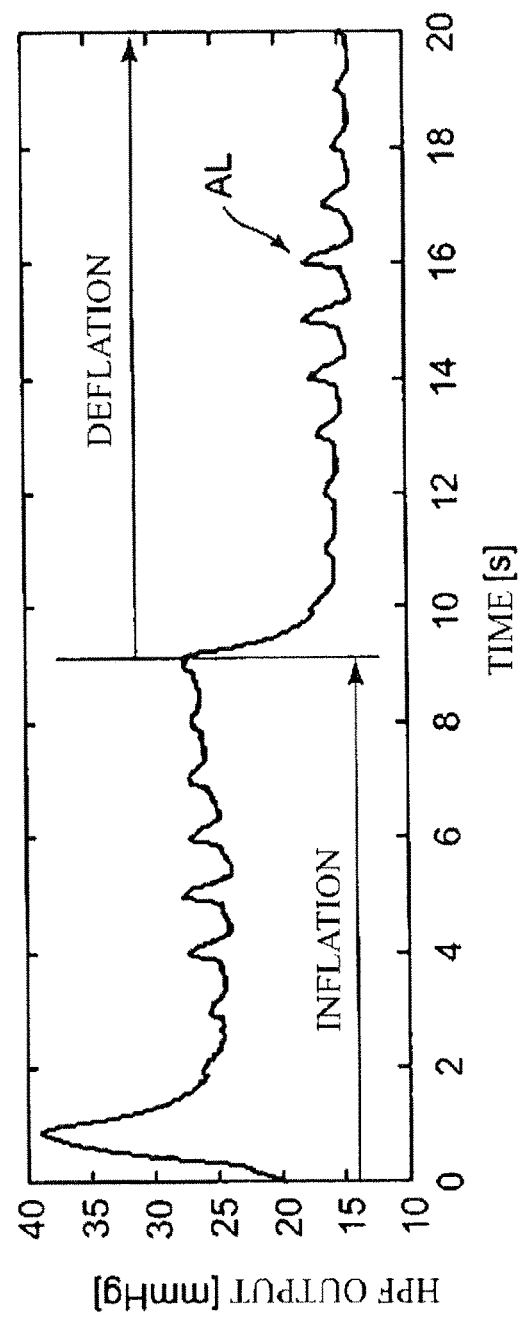
FIG. 9B is a diagram illustrating an example of a signal (HPF output) obtained by passing the aforementioned cuff pressure signal through a high pass filter.
Figure 10:
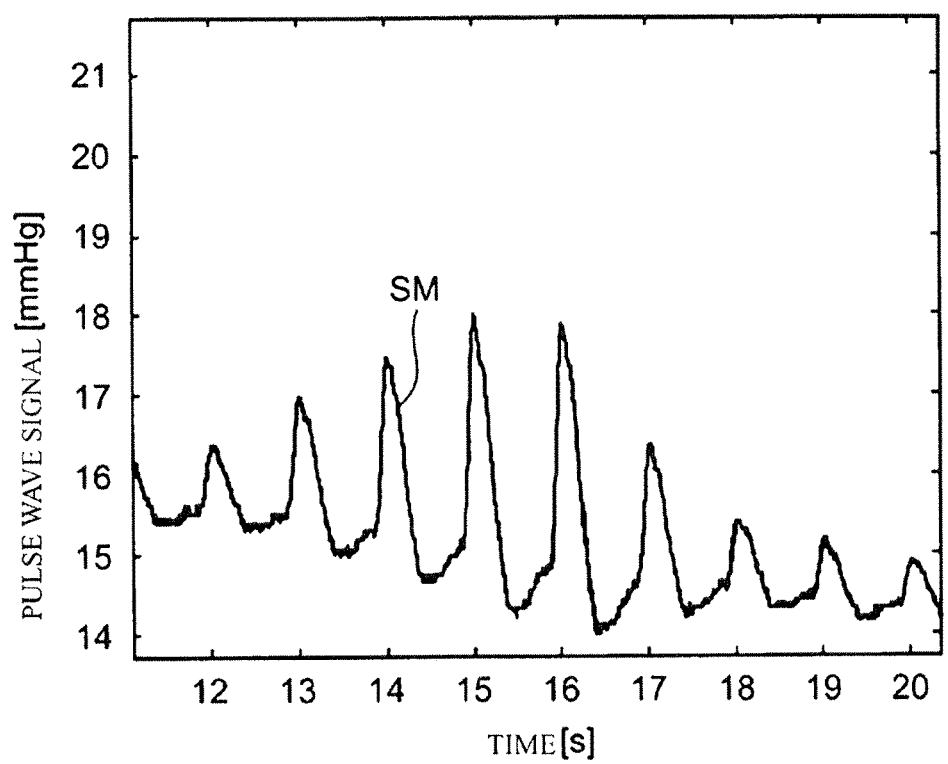
FIG. 10 is a diagram illustrating the signal of FIG. 9B in an enlarged manner during deflation, as an example of a pulse wave signal expressing a pulse wave at a measurement area.
Figure 11A:
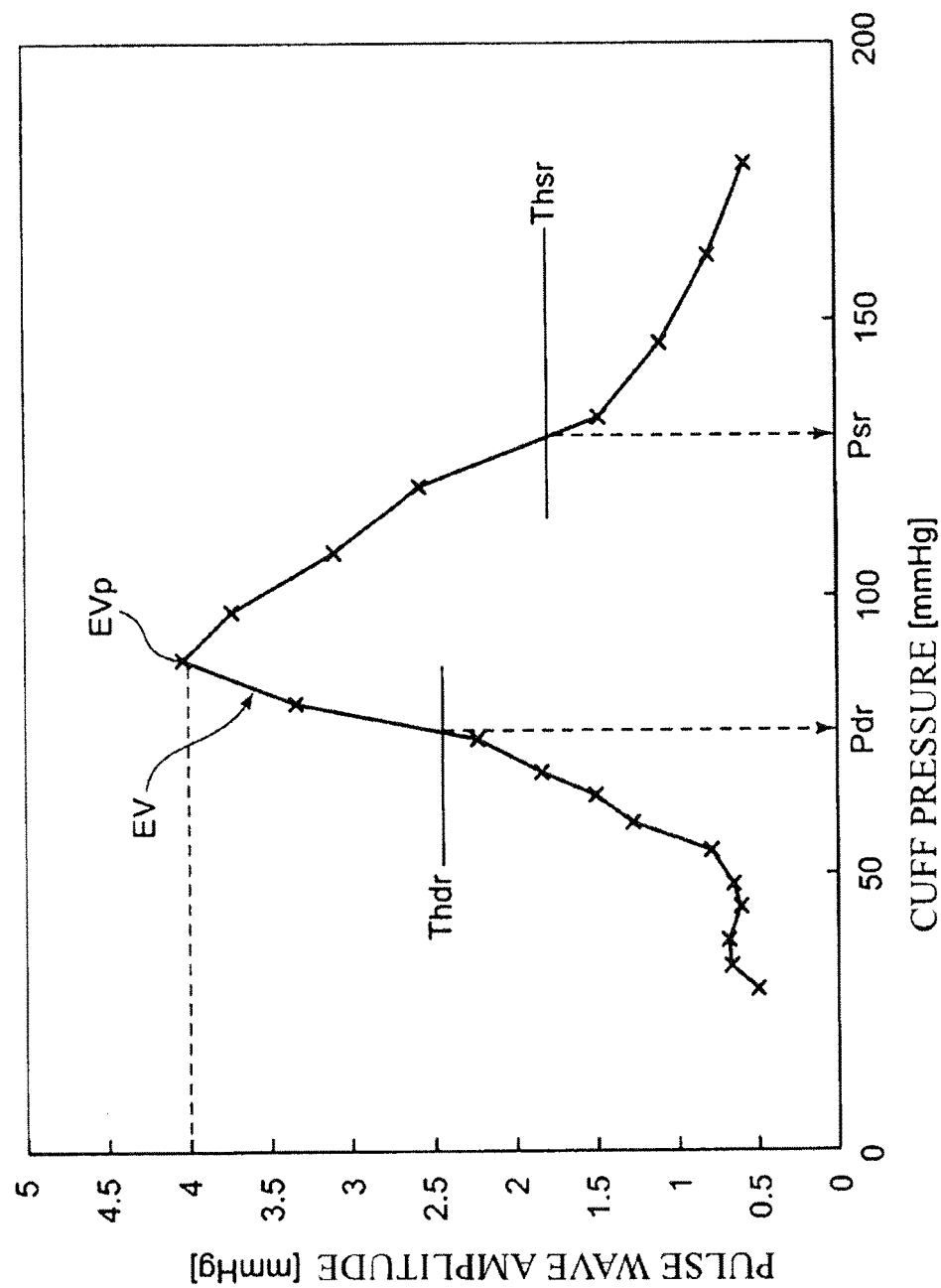
FIG. 11A is a diagram illustrating an envelope curve created using an amplitude string of the aforementioned pulse was signal, and a method for calculating a systolic blood pressure and a diastolic blood pressure of an adult using the stated envelope curve.
Figure 11B:
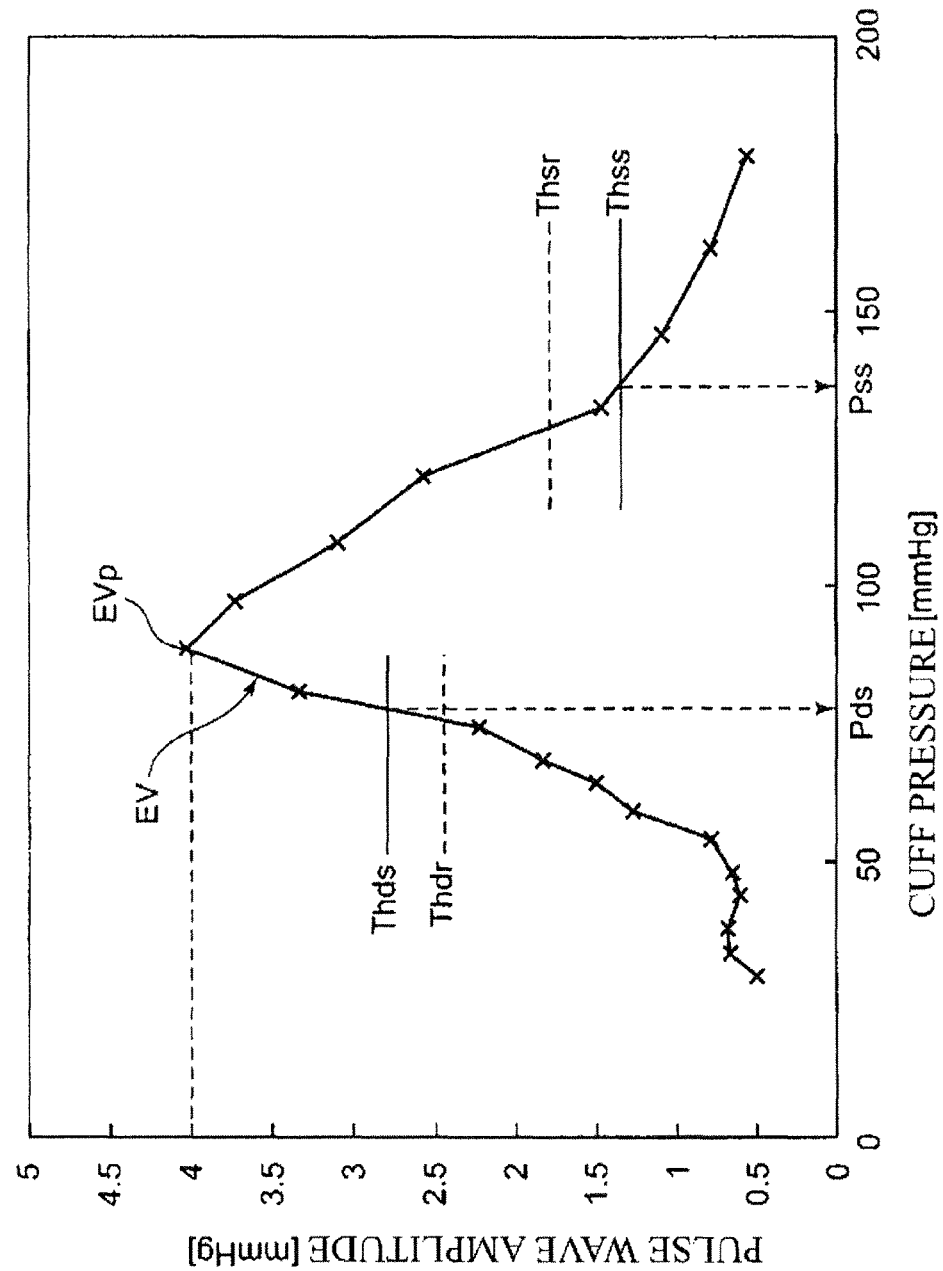
FIG. 11B is a diagram illustrating an envelope curve created using an amplitude string of the aforementioned pulse wave signal as an example, and a method for calculating a systolic blood pressure and a diastolic blood pressure of a child using the stated envelope curve.

An example of operations performed when the cuff type determining unit determines the connected cuff type in an initial period of cuff inflation immediately after blood pressure measurement is started, and the electronic blood pressure monitor 1 measures a blood pressure using a result of the determination, will be described next with reference to FIGS. 6 to 1B. FIG. 6 illustrates an operational flow of the to electronic blood pressure monitor 1. FIG. 7 illustrates an example of elements implemented by software executed by the CPU 100 of the electronic blood pressure monitor 1 for determining the cuff type and measuring a blood pressure value. In this example, the elements for determining the cuff type include a determination timing detecting unit 101, a plug inner pressure obtaining unit 103, a pump discharge pressure obtaining unit 102, a differential pressure calculating unit 104, and a cuff type determining unit 105. The elements for measuring a pulse wave and calculating a blood pressure value include a pulse wave amplitude string attaining unit 111, an envelope curve creating unit 112, a threshold level setting unit 113, a systolic blood pressure calculating unit 114, and a diastolic blood pressure calculating unit 115. FIGS. 8A and 8B respectively illustrate the flows of processes carried out when calculating blood pressure values using, a normal blood pressure measurement algorithm (a blood pressure measurement algorithm for a typical adult) or a blood pressure measurement algorithm for a child. FIG. 9A illustrates an example of a cuff pressure signal Pcf, and FIG. 9B illustrates an output example AL of a fluctuation component (pulse wave component) extracted from the cuff pressure signal Pcf by a high pass filter (HPF). FIG. 10 illustrates an example of a pulse wave signal SM generated from the output example AL, and FIGS. 11A and 11B illustrate envelope curves EV generated from the pulse wave signal SM.

Note that the following example assumes that two types of cuffs are present, one being a cuff for a typical adult, to which the type I plug 231 is connected, and the other being a cuff for a child, to which the type II plug 232 is connected. That the cuff for a typical adult includes the type I plug 231 and the cuff for a child includes the type II plug 232 is held in the memory 61 or the like in advance as data.

Generally speaking, the following operations are carried out in the case of measuring a blood pressure through a typical oscillometric method. The cuff is first wrapped around a measurement area an arm or the like) of a measurement subject, and during measurement, the cuff pressure is increased beyond a systolic blood pressure and then gradually reduced by controlling a pump and a valve. The cuff pressure is detected by a pressure sensor as the pressure drops, and variations in an arterial volume arising in an artery in the measurement area are extracted as a pulse wave signal. A maximum blood pressure (systolic blood pressure) and a minimum blood pressure (diastolic blood pressure) are then calculated on the basis of a change (primarily a rise and a fall) in the amplitude of the pulse wave signal accompanying a change in the cuff pressure at that time.

In this electronic blood pressure monitor 1 the blood pressure value of a measurement subject is measured by the CPU 100 through an oscillometric method, in accordance with the flow illustrated in FIG. 6.

Specifically, when the power switch 63A has been turned on and the measure switch 63B is pressed, the blood pressure monitor 1 starts the blood pressure measurement, as indicated in FIG. 6. At the start of the blood pressure measurement, the CPU 100 resets a processing memory region, and outputs a control signal to the valve driving circuit 540. On the basis of the control signal, the valve driving circuit 540 opens the valve 54 and exhausts the air from within the fluid bladder 21 of the cuff 20. Next, control for adjusting the first pressure sensor 51 and the second pressure sensor 52 to 0 mmHg is carried out.

Upon the blood pressure measurement starting, the CPU 100 first closes the valve 54 using the valve driving circuit 540, and then carries out control for supplying air to the fluid bladder 21 by driving the pump 53 using the pump driving circuit 530. As a result, the fluid bladder 21 is inflated and the cuff pressure gradually increases (step ST1).

Operating as the determination timing detecting unit 10 (FIG. 7) the CPU 100 determines whether or not 0.3 seconds have passed following the start of inflation (step ST2).

When it is determined that 0.3 seconds have passed following the start of inflation (YES in step ST2) the CPU 100 operates as the plug inner pressure obtaining unit 103 (FIG. 7 and obtains the inner pressure (cuff pressure) of the plug (231 or 232) of the connected cuff 20 using the second oscillation circuit 520, and the CPU 100 also operates as the pump discharge pressure obtaining unit 102 (FIG. 7) and obtains the pressure in the first pipe 31 (the pump discharge pressure) using the first oscillation circuit 510. Then, operating as the differential pressure calculating unit 104 (FIG. 7), the CPU 100 calculates the differential pressure (=pump discharge pressure−cuff pressure (plug inner pressure)) (step ST3).

Operating as the cuff type determining unit 105 (FIG. 7), the CPU 100 determines whether or not the calculated differential pressure is greater than or equal to 4 mmHg (step ST4).

In the case where the differential pressure is greater than or equal to 4 mmHg (YES in step ST4), the cuff type determining unit 105 (FIG. 7) determines that the plug connected to the connector 30 is the type II plug 232, and thus determines that the connected cuff 20 is a cuff for a child (step ST5).

In the case where the differential pressure is less than 4 mmHg (NO in step ST4), the cuff type determining unit 105 (FIG. 7) determines that the plug connected to the connector 30 is the type I plug 231, and thus determines that the connected cuff 20 is not a cuff for a child (that is, is a cuff for a typical adult) (step ST6).

The electronic blood pressure monitor 1 derives an appropriate inflation rate on the basis of the determination result from step ST5 or step ST6, and continues to inflate the cuff at that rate. Once the cuff pressure is increased and reaches a predetermined pressure (YES in step ST7), the CPU 100 stops the pump 53 using the pump driving circuit 530, and then carries out control for gradually opening the valve 54 using the valve driving circuit 540. As a result, the fluid bladder 21 is deflated and the cuff pressure gradually decreases (step ST8).

Here, the predetermined pressure is a pressure significantly higher than the systolic blood pressure of the measurement subject (systolic blood pressure+30 mmHg, for example), and is either stored in the memory 61 in advance, or is determined by the CPU 100 estimating the systolic blood pressure through a predetermined formula as the cuff pressure increases (see JP 2001-70263A, for example). With respect to the rate of deflation, a target deflation rate serving as a target is set while the cuff is being inflated, and the CPU 100 controls how far the valve 54 is opened so as to achieve that target deflation rate (see the aforementioned document). Note that the CPU 100 takes into consideration the determination result from step ST5 or step ST6 when setting the rate of deflation.

Next, the CPU 100 refers to the determination result from step ST5 or step ST6, and determines the blood pressure measurement algorithm to use to calculate the blood pressure value. In the case where the connected cuff 20 is a cuff for a typical adult NO in step ST9), a normal that is, for a typical adult) blood pressure measurement algorithm is selected as the blood pressure measurement algorithm (step ST11), whereas in the case where the connected cuff 20 is a cuff for a child (YES in step S19), a blood pressure measurement algorithm for a child is selected.

In the aforementioned deflation process, the second pressure sensor 52 for the first pressure sensor 51) detects the cuff pressure signal (indicated by Pcf (FIGS. 8A, 8B, and 9A)) expressing the pressure in the cuff 20, via the cuff 20. On the basis of this cuff pressure signal Pcf, the CPU 100 calculates the blood pressure values (systolic blood pressure and diastolic blood pressure) through an oscillometric method by employing an algorithm that will be described later (step ST11 or ST10). Note that the blood pressure value calculation is not limited to being carried out during deflation, and may be carried out during inflation.

In the case where the normal blood pressure measurement algorithm has been selected (NO in step ST9), the blood pressure value is calculated in step ST11. The calculation of the blood pressure Value using the normal blood pressure measurement algorithm (step ST11) will be described next with reference to FIGS. 7, 8A, 9A 9B, 10, and 11A.

In this case, first, as indicated in FIG. 8A, the pulse wave amplitude string obtaining unit 111 (FIG. 7) takes the cuff pressure signal Pcf detected by the second pressure sensor 52 (or first pressure sensor 51) as described above and extracts the pulse wave signal SM, which expresses a pulse wave in the measurement area, and is superimposed on the cuff pressure signal Pcf.

Here, as indicated in FIG. 9A, the cuff pressure signal Pcf is a signal in which a variation component caused by a change in arterial volume occurring with each beat is superimposed on the pressure that increases (during inflation) or decreases (during deflation substantially linearly as time passes. The pulse wave amplitude string obtaining unit 111 extracts a fluctuation component (HPF output) such as that indicated in FIG. 9B, extracted from the cuff pressure Signal Pcf through a high pass filter (HPF), and outputs that component as the pulse wave signal SM, as indicated in FIG. 10. In this example, in response to changes in the arterial volume, the pulse wave signal SM begins to increase approximately 12 seconds after the start of measurement, reaches a maximum at approximately 16 seconds, and almost completely disappears at approximately 20 seconds, as indicated in FIG. 10 (corresponding to deflation).

The pulse wave amplitude string obtaining unit 111 then obtains a string AL (FIG. 9B) of the amplitude expressed by the pulse wave signal SM (called a "pulse wave amplitude" as appropriate hereinafter).

Next, as indicated in FIG. 8A, the envelope curve creating unit 112 in FIG. 7 creates an envelope curve EV connecting the amplitudes in the pulse wave amplitude string AL obtained 1w the pulse wave amplitude string obtaining unit 111 FIG. 11A).

In order to find a systolic blood pressure BPsys and a diastolic blood pressure BPdia (FIG. 8A), the threshold level setting unit 113 calculates and sets a first adult-use to threshold level Thsr and a second adult-use threshold level Thdr that are each a predetermined percentage of the value of a maximum peak EVp in the envelope curve EV. In this example, the first adult-use threshold level Thsr is set to approximately 40% of the value of the maximum peak EVp, and the second adult-use threshold level Thdr is set to approximately 60% of the value of the maximum peak EVp.

Next, as indicated in FIGS. 8A and 11A, the systolic blood pressure calculating unit 114 (FIG. 7) finds a pressure value Psr at a point where a part of the envelope curve EV on the higher-pressure side of the maximum peak EVp crosses the first adult-use threshold level Thdr, and calculates that value as the systolic blood pressure BPsys. In addition as indicated in FIGS. 8A and 11A, the diastolic blood pressure calculating unit 115 in FIG. 7 finds a pressure value Pdr at a point where the part of the envelope curve EV on the lower-pressure side of the maximum peak EVp crosses the second adult-use threshold level Thdr, and calculates that value as the diastolic blood pressure BPdia.

Although the first adult-use threshold level Thsr is set to approximately 40% of the value of the maximum peak EVp and the second adult-use threshold level Thdr is set to approximately 60% of the value of the maximum peak EVp in the above example, the thresholds are not limited thereto.

On the other hand, in the case where the child blood pressure measurement algorithm has been selected (YES in step ST9), the blood pressure value is calculated in step ST10 using the child blood pressure measurement algorithm. The calculation of the blood pressure value using the child blood pressure measurement algorithm (step ST10 will be described next with reference to FIGS. 7, 8B, 9A, 98, 10, and 11B. In the following example, the child blood pressure measurement algorithm and the normal blood pressure measurement algorithm differ in terms of the settings of thresholds for finding the systolic and diastolic blood pressures, for example, but are the same in other respects. This is based on examples showing that a child's blood pressure will be calculated lower than normal (approximately 10 to 20 mmHg lower, for example) in the case where the blood pressure value is calculated using a normal (that is, for an adult) blood pressure measurement algorithm. However, depending on the blood pressure measurement algorithm, there have also been reports of a child's blood pressure being calculated higher than the actual blood pressure value in the case where the child's blood pressure is measured using a blood pressure measurement algorithm for a typical adult. The following merely describes an example, and can be changed as appropriate.

In this case as well, first, as indicated in FIG. 8B, the pulse wave amplitude string obtaining unit 111 (FIG. 7) takes the cuff pressure signal Pcf detected by the second pressure sensor 52 (or first pressure sensor 51) as described above and extracts the pulse wave signal SM, which expresses a pulse wave in the measurement area and overlaps the cuff pressure signal Pcf; then, the envelope curve creating unit 112 creates the envelope curve EV (FIG. 11B).

In order to find the systolic blood pressure BPsys and the diastolic blood pressure BPdia (FIG. 8B), the threshold level setting unit 113 calculates and sets a first child-use threshold level Thss and a second child-use threshold level Thds that are each a predetermined percentage of the value of the maximum peak EVp in the envelope curve EV. In this example, the first child-use threshold level Thss is set to approximately 35% of the value of the maximum peak EVp, and the second child-use threshold level Thds is set to approximately 65% of the value of the maximum peak EVp. As indicated in FIGS. 8B and 11B, the systolic blood pressure calculating unit 114 (FIG. 7) finds a pressure value Ps at a point where a part of the envelope curve EV on the higher-pressure side of the maximum peak EVp crosses the first child-use threshold level Thss, and calculates that value as the systolic blood pressure BPsys. In addition, as indicated in FIGS. 8B and 11B, the diastolic blood pressure calculating unit 115 in FIG. 7 finds a pressure value Pds at a point where the part of the envelope curve EV on the lower-pressure side of the maximum peak EVp crosses the second child-use threshold level Thds, and calculates that value as the diastolic blood pressure BPdia. Although the first child-use threshold level Thss is set to approximately 35% of the value of the maximum peak EVp and the second child-use threshold level Thds is set to approximately 65% of the value of the maximum peak EVp in the above example, the thresholds are not limited thereto.

Once the blood pressure value has been calculated and determined, the CPU 100 carries out control for displaying, the calculated blood pressure value in the display unit 62 (step ST12) and storing the blood pressure value in the memory 61 (step ST13).

Next, upon the stop switch 63C being pressed, the CPU 100 carries out control for opening the valve 54 using the valve driving circuit 540 and exhausting the air from within the fluid bladder 21 of the cuff 20 (step ST14).

Then, upon the power switch 63A being pressed, the blood pressure measurement ends.

In this manner, the electronic blood pressure monitor 1 can accurately and quickly determine the type of a cuff connected to a main unit with a simple configuration and using a simple process. This determination can be carried out during the process of inflation for measuring the blood pressure, for example, and thus the length of the inflation process is not increased for the purpose of determining the cuff type. The result of the cuff type determination is then applied in subsequent inflations and deflations, in optimizing the blood pressure measurement algorithm, and so on. This feature gives the electronic blood pressure monitor 1 superior usability.

The electronic blood pressure monitor according to this invention may measure other biological information, such as a pulse rate or the like, in addition to measuring the blood pressure value.

The above-described embodiment is merely an example, and various modification can be made thereon without departing from the scope of this invention.

REFERENCE SIGNS LIST 1 electronic blood pressure monitor
10 electronic blood pressure monitor main u
20 blood pressure measurement cuff
23 plug
30 connector (plug receiving portion)
23a O-ring. (sealing member)
23b fluid supply/exhaust hole
23c detection hole (through-bole)
30a O-ring (sealing member)
40 connection portion
51 first pressure sensor (pump discharge pressure sensor)
52 second pressure sensor (plug inner pressure (cuff pressure) sensor)
100 CPU

The invention claimed is:

1. An electronic blood pressure monitor comprising a cuff configured to pressurize a measurement area and a main unit that measures a pressure in the cuff and calculates a blood pressure in the measurement area on the basis of a result of the measured pressure,
wherein the cuff includes:
a fluid bladder;
a tube that communicates with the fluid bladder; and
an approximately cylindrical plug, attached to a leading end of the tube, that is to be inserted into the main unit to supply a fluid to the fluid bladder, and
a through-hole provided in a peripheral wall of the plug;
wherein an inner diameter of a part of the plug further on a leading end side of the plug than the through-hole is set variably, in accordance with a type of the cuff, to a diameter less than or equal to an inner diameter of a part of the plug other than the part further on the leading end side, and
wherein the main unit includes:
a plug receiving portion that communicates with a pump within a housing of the main unit via a pipe;
a first pressure sensor that detects a pressure in the pipe;
a second pressure sensor that detects an inner pressure of the plug inserted into the plug receiving portion, through the through-hole in the plug; and
a cuff type determining unit that determines the type of the cuff connected to the main unit on the basis of a difference between the pressures detected by the first pressure sensor and the second pressure sensor.

2. The electronic blood pressure monitor according to claim 1, further comprising:
a sealing member that seals a gap between a part of an outer circumferential surface of the plug located further on the leading end side of the plug than the through-hole and an inner circumferential surface of the plug receiving portion in an airtight manner.

3. The electronic blood pressure monitor according to claim 2,
wherein the inner diameter of the part of the plug further on the leading end side of the plug than the through-hole is set variably in accordance with a capacity of the fluid bladder contained in the cuff.

4. The electronic blood pressure monitor according to claim 3,
wherein the cuff type determining unit determines the type of the cuff on the basis of a difference between the detected pressures when a change over time in the difference between the pressures, arising due to the pump starting to inflate the cuff, is in a plateau state.

5. The electronic blood pressure monitor according to claim 4,
wherein the cuff type determining unit carries out the determination by comparing the difference between the pressures detected by the first pressure sensor and the second pressure sensor with a predetermined threshold.

6. The electronic blood pressure monitor according to claim 3,
wherein the cuff type determining unit carries out the determination by comparing the difference between the pressures detected by the first pressure sensor and the second pressure sensor with a predetermined threshold.

7. The electronic blood pressure monitor according to claim 2,
wherein the cuff type determining unit determines the type of the cuff on the basis of a difference between the detected pressures when a change over time in the difference between the pressures, arising due to the pump starting to inflate the cuff, is in a plateau state.

8. The electronic blood pressure monitor according to claim 7,
wherein the cuff type determining unit carries out the determination by comparing the difference between the pressures detected by the first pressure sensor and the second pressure sensor with a predetermined threshold.

9. The electronic blood pressure monitor according to claim 2,
wherein the cuff type determining unit carries out the determination by comparing the difference between the pressures detected by the first pressure sensor and the second pressure sensor with a predetermined threshold.

10. The electronic blood pressure monitor according to claim 1,
wherein the inner diameter of the part of the plug further on the leading end side of the plug than the through-hole is set variably in accordance with a capacity of the fluid bladder contained in the cuff.

11. The electronic blood pressure monitor according to claim 10,
wherein the cuff type determining unit determines the type of the cuff on the basis of a difference between the detected pressures when a change over time in the difference between the pressures, arising due to the pump starting to inflate the cuff, is in a plateau state.

12. The electronic blood pressure monitor according to claim 11,
wherein the cuff type determining unit carries out the determination by comparing the difference between the pressures detected by the first pressure sensor and the second pressure sensor with a predetermined threshold.

13. The electronic blood pressure monitor according to claim 10,
wherein the cuff type determining unit carries out the determination by comparing the difference between the pressures detected by the first pressure sensor and the second pressure sensor with a predetermined threshold.

14. The electronic blood pressure monitor according to claim 1,
wherein the cuff type determining unit determines the type of the cuff on the basis of a difference between the detected pressures when a change over time in the difference between the pressures, arising due to the pump starting to inflate the cuff, is in a plateau state.

15. The electronic blood pressure monitor according to claim 14,
wherein the cuff type determining unit carries out the determination by comparing the difference between the pressures detected by the first pressure sensor and the second pressure sensor with a predetermined threshold.

16. The electronic blood pressure monitor according to claim 1,
wherein the cuff type determining unit carries out the determination by comparing the difference between the pressures detected by the first pressure sensor and the second pressure sensor with a predetermined threshold.

17. A cuff type determination method that determines a type of a cuff connected to the main unit in the electronic blood pressure monitor according to claim 1, the method comprising:
a step of driving the pump to start inflating the cuff;
a step of detecting a pressure within the pipe using the first pressure sensor and detecting an inner pressure in the plug using the second pressure sensor; and
a step of the cuff type determining unit determining the type of the connected cuff on the basis of a difference in the pressures detected by the first pressure sensor and the second pressure sensor in the step of detecting.

* * * * *